(12) United States Patent
Thorpe

(10) Patent No.: US 6,189,538 B1
(45) Date of Patent: Feb. 20, 2001

(54) TOURNIQUET AND METHOD OF USING

(76) Inventor: Patricia E. Thorpe, 10009 Fieldcrest Dr., Omaha, NE (US) 68114

(*) Notice: Under 35 U.S.C. 154(b), the term of this patent shall be extended for 0 days.

(21) Appl. No.: 08/753,001

(22) Filed: Nov. 19, 1996

Related U.S. Application Data

(60) Provisional application No. 60/007,369, filed on Nov. 20, 1995.

(51) Int. Cl.$^7$ .................................................... A61B 19/00
(52) U.S. Cl. .......................... 128/898; 606/203; 606/201
(58) Field of Search ................... 606/191–200; 128/898

(56) References Cited

U.S. PATENT DOCUMENTS

| | | | |
|---|---|---|---|
| 3,586,001 | * | 6/1971 | Sanderson ............................ 606/203 |
| 4,182,338 | * | 1/1980 | Stanulis ................................ 606/203 |
| 4,944,289 | * | 7/1990 | Matthews ............................. 606/204 |
| 4,997,438 | * | 3/1991 | Nipper ................................. 606/204 |
| 5,295,996 | * | 3/1994 | Blair .................................... 606/203 |
| 5,512,056 | * | 4/1996 | Stevens et al. ...................... 606/203 |
| 5,695,520 | * | 12/1997 | Bruckner et al. ................... 606/201 |
| 5,848,981 | * | 12/1998 | Herbranson ......................... 606/204 |
| 5,873,890 | * | 2/1999 | Porat ................................... 606/201 |

* cited by examiner

Primary Examiner—Glenn K. Dawson
(74) Attorney, Agent, or Firm—Benjamin Aaron Adler

(57) ABSTRACT

A non-pneumatic tourniquet for use in treating deep vein thrombosis including: a band, the band having a first end and a second end, wherein said first end and said second end have structure for adjustably connecting to one another; and an adjustable disc, the disc made of substantially hard, non-compressable material and wherein said disc is adjustably connected to said band. A method of treating deep vein thrombosis is also disclosed in which the thrombus can not be easily treated using a catheter, i.e., actively lysed by flow-directed therapy.

7 Claims, 14 Drawing Sheets

TOURNIQUET AND METHOD OF USING

This application claims the benefit of U.S. Provisional No. 60/007,369 filed Nov. 20, 1995.

BACKGROUND OF THE INVENTION

1. Field of the Invention

The present invention relates generally to the fields of interventional radiology, vascular surgery, cardiology, oncology and medical devices. More specifically, the present invention relates to a novel tourniquet and novel methods for its use.

2. Description of the Related Art

The use of systemic thrombolytic agents to treat deep vein thrombosis (DVT) has been reported previously.[1–5] While these investigations have demonstrated a certain degree of efficacy, the combination of high doses of a thrombolytic agent and the prolonged infusion times necessary to lyse venous clots have raised different safety concerns and limited acknowledgment of thrombolytic therapy as a viable treatment for deep vein thrombosis.[6] This method has had limited success in treating extremity deep vein thrombosis because collateral pathways become the preferred routes of venous outflow, and relatively little thrombolytic agent reaches the thrombus. However, because early clot lysis and re-opening of occluded veins can preserve venous valves and thus prevent or mitigate the development of chronic venous insufficiency,[7,8] investigators have persevered in their attempts to discover safer ways to lyse deep venous thrombi. Early lysis of arterial occulsions has been achieved by using local delivery, instead of systemic infusion of the thrombolytic agent.[9–12] Bleeding complications have remained low compared to systemic infusions.

Using this same treatment philosophy, a few preliminary investigations have successfully used local catheter-directed delivery of a thrombolytic agent to lyse venous clots in the subclavian/axillary veins,[13–17] and more recently in the iliofemoral segment of the lower extremity.[18–24] The results from these preliminary trials have shown improved efficacy and safety of locally-delivered thrombolytic therapy for the treatment of deep vein thrombosis. Thrombus not in easy reach of catheters, however, has not been easily and successfully treated.

The prior art is deficient in the lack of effective means of treating deep vein thrombosis in which the thrombus can not be easily treated using a catheter. The present invention fulfills this longstanding need and desire in the art.

SUMMARY OF THE INVENTION

The present invention provides an effective means of treating deep vein thrombosis in which the thrombus cannot be easily treated using a catheter; i.e., actively lysed by flow-directed therapy. In some cases the flow-directed technique is sufficient to remove thrombus and in other situations, flow-directed infusion is an important adjunct to catheter-directed delivery. Described here is the flow-directed infusion technique for treatment of deep vein thrombosis using pedal assess.

The value of flow-directed thrombolysis derives from the principle that systemic blood flow follows the path of least resistance. The technique of redirecting venous flow with a strategically placed tourniquet provides an effective means of delivering a lytic agent to thrombotic deep veins in the lower extremity. In this manner, venous flow remains imperceptable with duplex and standard venography but becomes a vehicle for delivery of the lytic agent to obstructed vessels. This is a particular advantage when occluded veins are not accessible to catheters, or where catheter placement is difficult or undesired. The involvement of multiple infrapopliteal veins, causing significant impedance to venous outflow, cannot be effectively treated with a single catheter. More often, with multi-segmental venous thrombosis, it is important to mobilize the flow in both the iliofemoral and popliteal tibial areas simultaneously in order to reach a satisfactory outcome. The flow-directed method delivers a high concentration of urokinase to thrombosed deep veins via small pedal cannula. The catheter-directed infusion in the iliac and femoral veins may be combined with a pedal infusion when there is significant occlusive thrombus throughout the extremity. Simultaneous infusions are complimentary and result in more rapid treatment of extensive multi-segmental thrombus. The pedal infusion is effective when used alone for short-segment femoral popliteal and infrapopliteal thrombosis. Research continues to indicate the importance of the posterior tibial valves. Lysis of thrombus in these veins may be significant for preventing post-thrombotic syndrome.

In one aspect of the present invention, there is provided a non-pneumatic tourniquet for use in treating deep vein thrombosis comprising: a band, said band having a first end and a second end, wherein said first end and said second end have means for adjustably connecting to one another; and an adjustable disc, said disc comprised of substantially hard, non-compressable material and wherein said disc is adjustably connected to said band.

In another aspect of the present invention, there is provided a method of treating deep vein thrombosis in which the thrombus cannot be easily treated using a catheter, i.e., actively lysed by flow-directed therapy. To this end, one embodiment of the present invention is drawn to a method for treating deep vein thrombosis, comprising the steps of: placing an intravenous needle in a vein in an area to be treated; determining a pattern of venous blood flow in said area to be treated; securing a tourniquet around said area to be treated, wherein a disc of said tourniquet is positioned over said vein so as to apply pressure to said vein; checking re-direction of blood flow through said area to be treated; infusing said vein through said needle; releasing said tourniquet after an appropriate period of time; and re-securing said tourniquet after an appropriate period of time. To illustrate a detailed example of one embodiment of a method of using the novel tourniquet of the present invention, 1) a small gauge intravenous needle is placed in the dorsal vein of the foot; 2) radioopaque contrast media ("dye") is injected usually under fluoroscopy to determine the venous anatomy and pattern of venous blood flow; 3) the tourniquet is secured just about the inner ankle bone with the capped disc positioned at the location of the saphenous vein; 4) using fluoroscopy, one then confirms the effective redirecting of contrast into the deep middle veins of the leg; 5) skin is marked to designate the proper location if disc placement as well as tourniquet level; 6) a urokinase infusion is connected to pedal IV the site for continuous "flow-directed" infusion; and 7) release the tourniquet is released 10 minutes/hour and replaced.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention are attained and can be understood in detail, more particular descriptions of the invention briefly summarized above may be had by reference to certain embodiments which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
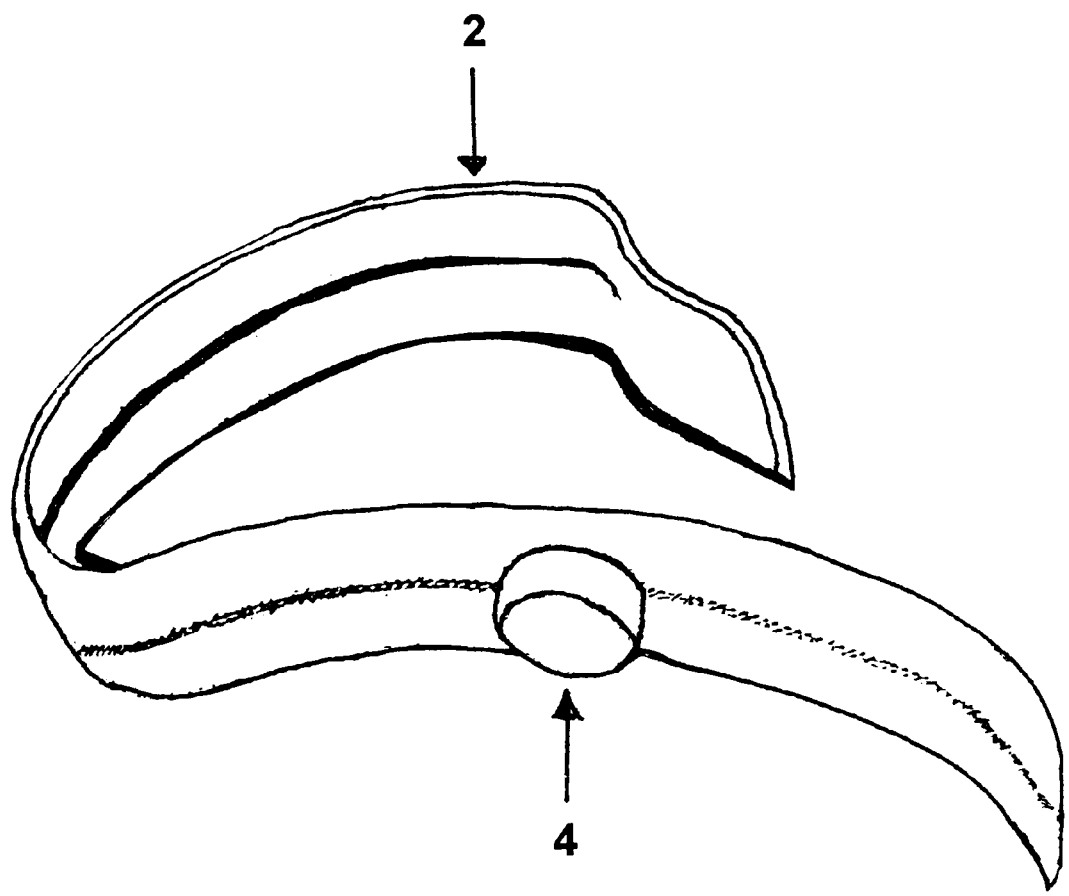
FIGS. 1A and 1B show schematics of the tourniquet of the present invention illustrating the various components thereof.

The present invention is directed to a novel tourniquet useful for flow-directed thrombolysis. With reference now to the Figures, FIG. 1A shows a schematic diagram of the tourniquet body (2) of the present invention. The tourniquet body (2) itself may be manufactured of any of several elastic or non-elastic type materials known in the art. Preferably, the tourniquet body (2) is made of nylon, rayon, or a cotton blend material. Although the tourniquet of the present invention may be any length and width which allows for its successful use in flow-directed thrombolysis, the tourniquet body (2) preferably has a length of from about 8 inches to about 25 inches and a width of from about 1 inch to about 5 inches. Most preferably, the tourniquet body (2) has a width of about 1.5 inches.

Strategically placed on one end of the tourniquet body (2) of the present invention is an adjustable disc (4). The disc is comprised of a substantially hard, non-compressable material and the disc is adjustably connected to the band. The disc (4) may be attached to the tourniquet body (2) by velcro or other means well known to those having ordinary skill in this art. One side of the disc is adhered to a velcro hook that will let the disc be repositioned. The disc (4) may be composed of any of several hard materials which allows the disc to provide focal point compression when applied with the band or tourniquet.

Preferably, the disc (4) is made of a synthetic rubber but could be made of various other materials including sponge, silicone and clay. The diameter of the disc (4) is from about 0.5 inches to about 2.0 inches. Preferably, the diameter of the disc (4) is from about 1 inch to about 1.5 inches. The thickness of the disc (4) is generally from about 0.25 inches to about 0.5 inches. Preferably, the thickness of the disc (4) is about 0.31 inches when the diameter of the disc (4) is about 1.06 inches.

Figure 1B:
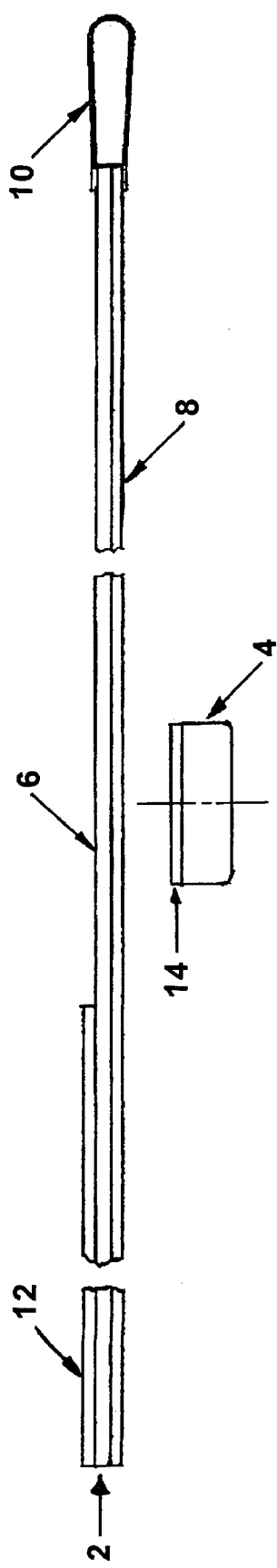

FIG. 1B shows a side view of the tourniquet body (2) of the present invention. FIG. 1 shows that the tourniquet body (2) is composed of an elastic band (6) and a loop layer (8). The elastic band (6) permits the tourniquet body (2) to be adjusted to the size of the ankle or leg and applied tightly enough to compress the vein but not so as to diminish arterial flow. Arterial flow may be determined by a palpable popliteal dorsalis pedis pulse or doppler signal.

FIG. 1B also illustrates other various components of the tourniquet body (2). In addition to showing the elastic band (6) and a loop layer (8), FIG. 1B shows a label (10) which functions to identify the tourniquet. Attached to the elastic band (6) is a hook strip (12) which is used to adjust the applied length. Also illustrated on FIG. 1 is the disc (4) which is connected to the tourniquet body (2) by means of a hook piece (14). Preferably, the hook piece (14) is composed of well-adhered velcro.

Figure 1C:
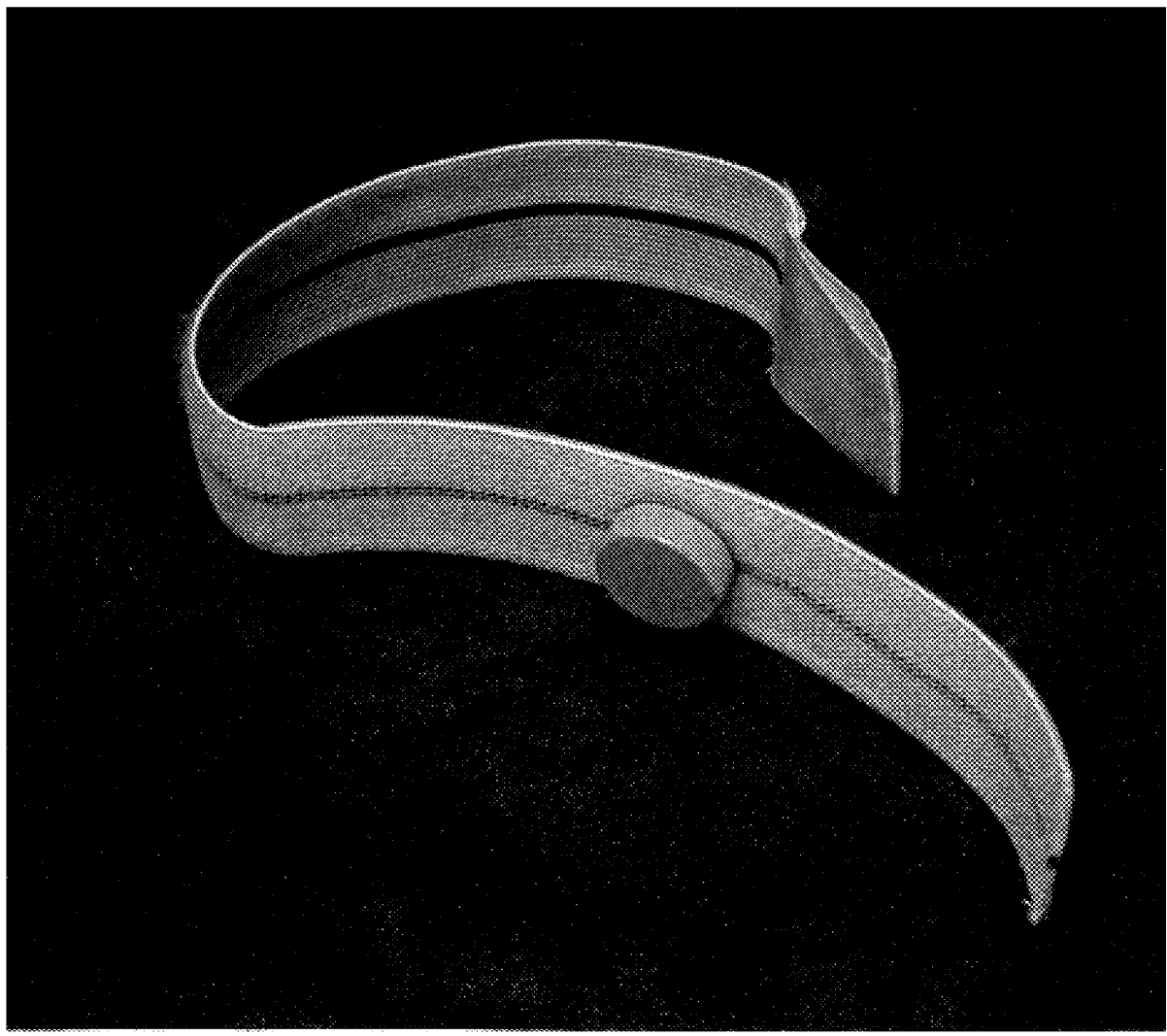
FIG. 1C is a photo of the tourniquet.

The present invention also is directed to a method of decreasing flow for facilitating schlerotherapy. FIG. 1C shows a photograph of a preferred tourniquet of the present invention.

The following examples are given for the purpose of illustrating various embodiments of the invention and are not meant to limit the present invention in any fashion.

EXAMPLE 1

Principles

Flow-directed infusion of a thrombolytic agent to an occulsive thrombus in the leg is based on the principle that existing blood flow can carry lytic agents to affected veins and venules that are inaccessible to catheters. While residual blood flow may not be observable on ultrasound exam or venography, it nevertheless exists. This is the case even when the presenting limb is bluish in color, signaling phlegmasia cerulea dolens due to extensive compromise of venous outflow. With flow-directed therapy, blood is channeled by one or more strategically placed tourniquets into areas which otherwise appear totally occluded because of extensive proximal thrombus. Without tourniquets, blood flows to the path of least resistance. This is the remaining outflow which is frequently dominated by superficial veins emptying into the saphenous system. A catheter-directed infusion from a femoral or jugular approach is advised when there is significant thrombus in the iliac and femoral veins. A pedal infusion can supplement and is used where direct catheter access to the upper-leg deep veins is difficult or undesirable. Not infrequently, organized thrombus in the superficial femoral vein prohibits catheter passage distally. In cases where there is extensive infrainguinal and infrapopliteal thrombus, clearing of only the iliofemoral segment may not restore sufficient venous outflow from the leg to eliminate or mitigate symptoms. Moreover, even in the case of localized popliteal thrombosis, a flow-directed infusion effectively can remove acute clot in less than 12–24 hours, confirming that efficient delivery of lytic agents is achievable with this method.

EXAMPLE 2

Indications

Unless there is a contraindication to lytic therapy or anticoagulation, a pedal infusion with the flow-directed method will benefit the patient with thrombus in the deep veins of the calf, and/or extension into the popliteal and superficial femoral and iliac veins. When the saphenous system is involved, flow-directed thrombolytic therapy is ideal because there is no escape route through a path of least resistance, which in most instances of deep vein thrombosis is the saphenous vein.

EXAMPLE 3
Flow-Directed Infusion Procedure

When a clinical diagnosis suggests the presence of a deep vein thrombosis, objective assessment by means of ultrasound and/or venography should be performed. The diagnostic venogram is performed via a 22-gauge intercath placed in a dorsal foot vein of the affected limb, utilizing a 3-way stopcock and tubing extensions as shown in FIG. 1. The cannula can be placed retrograde or antegrade. Low osmolar contrast, 75 to 200 mL, is hand injected. The total volume depends on the creatinine and state of hydration. Under fluoroscopic visualization, the flow pattern into the superficial and deep system at the ankle and in the lower calf should be noted.

A velcro tourniquet is placed at the malleolar level, tight enough to compress the saphenous vein against the bone, thereby directing venous flow and "driving" contrast (and the lytic agent post-venogram) into the deep system of the calf. There may be some escape via perforators, but a second tourniquet at the femoral condyles can be used to promote flow into the tibial and popliteal superficial femoral vein system. After obtaining a baseline venogram, the location and extent of the thrombus can be assessed.

The thrombus load can be assessed objectively by grading segmental occlusion using a method developed and published by Marder.[25] To a large degree, when contrast can be demonstrated to flow into the deep system, urokinase and heparin can be delivered to the same location. Even if contrast is not seen, the flow-directed method can be effective because there is flow which is not appreciated. Documented flow on color Doppler or venography is not a prerequisite for an effective flow-directed infusion.

Figure 2A:
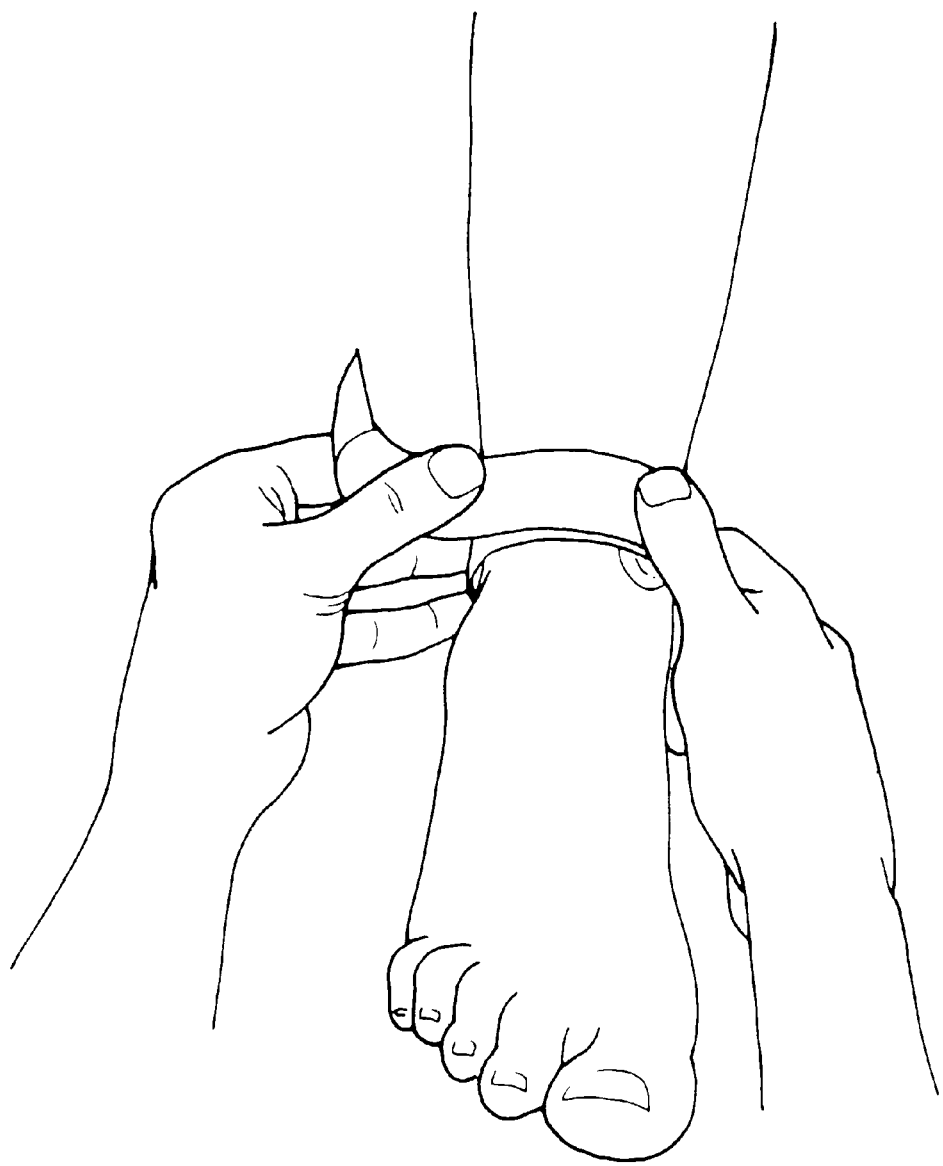
FIGS. 2A and 2B are diagrams of the placement of the tourniquet on the foot and the placement of pedal access for diagnostic venogram, flow-directed infusion.

The type of tourniquet and its correct placement in this procedure are important for effective treatment. Tourniquet placement too high on the ankle will be ineffective. Furthermore, many tourniquets (including blood pressure cuffs) are less comfortable and may cause blister formation and other pressure problems. Pneumatic compression boots can be used effectively to promote flow into the deep veins. After correct tourniquet placement, fluoroscopy is used to confirm the flow pattern and examine the insertion site for extravasation before beginning thrombolytic therapy. The pedal arch connects the superficial and deep venous systems in the foot. Focal compression of the greater saphenous vein near the malleolus can be accomplished with a small disk held in place by a tourniquet wide enough to displace pressure on soft tissue. Effective redirection of flow into the path of most resistance, i.e., the region of thrombosed deep veins, can be verified with contrast after the tourniquet is in place FIG. 2A. Furthermore, a myriad of veins are available for venous drug delivery. These are documented on the late phase images of an extremity venogram performed with high resolution digital subtraction technique using the Siemens Multistar.

A second velcro tourniquet at the condylar level can promote flow to the deep system to prolong contact of the lytic agent with infrapopliteal and popliteal thrombus and inhibit collateral steal into the saphenous system. The dorsalis pedis pulse should remain unchanged throughout the procedure, and the patient should not feel any tingling or numbness in the extremity. The tourniquet was released 15 minutes every hour. It is necessary to mark the skin to assure proper placement. Reduction in limb edema was monitored by obtaining baseline measurements of calf and thigh circumferences of both extremities pretreatment and then taking interval measurements every 12–24 hours.

EXAMPLE 4
Thrombolytic Mixture

Urokinase is preferred due to the low incidence of bleeding side effects, compared to streptokinase and to plasminogen activator.[2] Urokinase is reconstituted in 250–500 mL 0.9% normal saline (NS) to obtain a concentration of 1,000–2,000 IU/mL (i.e., 500,000 IU/500 cc NS=1000 IU/mL; 500,000 IU/250 cc NS=2000 IU/mL). Since it is preferable to have a sufficient volume running through the catheter to promote flow in a system that is already characterized by stasis, infusion through the pedal catheter should be 100,00–200,000 IU/hr. If there is a contraindication to saline, 5% dextrose in water ($D_5W$) can be used to reconstitute urokinase-however, this results in up to absorption of 20% urokinase into the plastic when diluted in concentrations of <5000 IU/cc. When depending on flow-directed infusion alone (no catheter-directed therapy above) 75–100 cc/hr of urokinase 2000 IU/cc should be infused. This will give an adequate dose (150,000–200,000 IU/hr) at a realistic infusion volume and rate. If combining flow-directed infusion with catheter-directed infusion in the femoral or iliac area, a divided dose is used (e.g., two infusions of 1000 IU/cc each are delivered at 75–100 cc/hr) to deliver 75,000–100,000 IU/hr through each infusion site. It should be kept in mind that venous thrombolytic infusions are prolonged and this protocol is designed to optimize the dose for a long, continuous infusion without risking events that would necessitate termination of therapy and inevitable rethrombosis if heparin as well as urokinase is discontinued.

EXAMPLE 5
Heparin

Figure 2B:
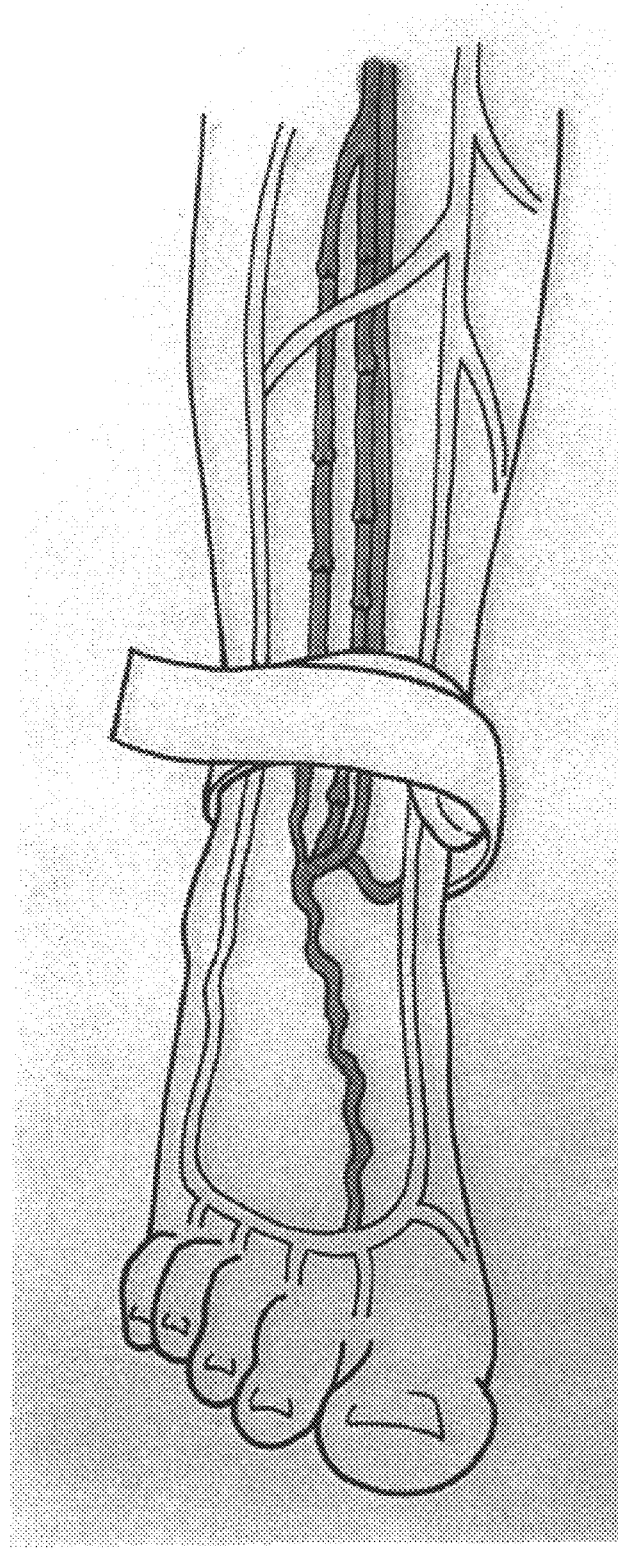
Figure 3:
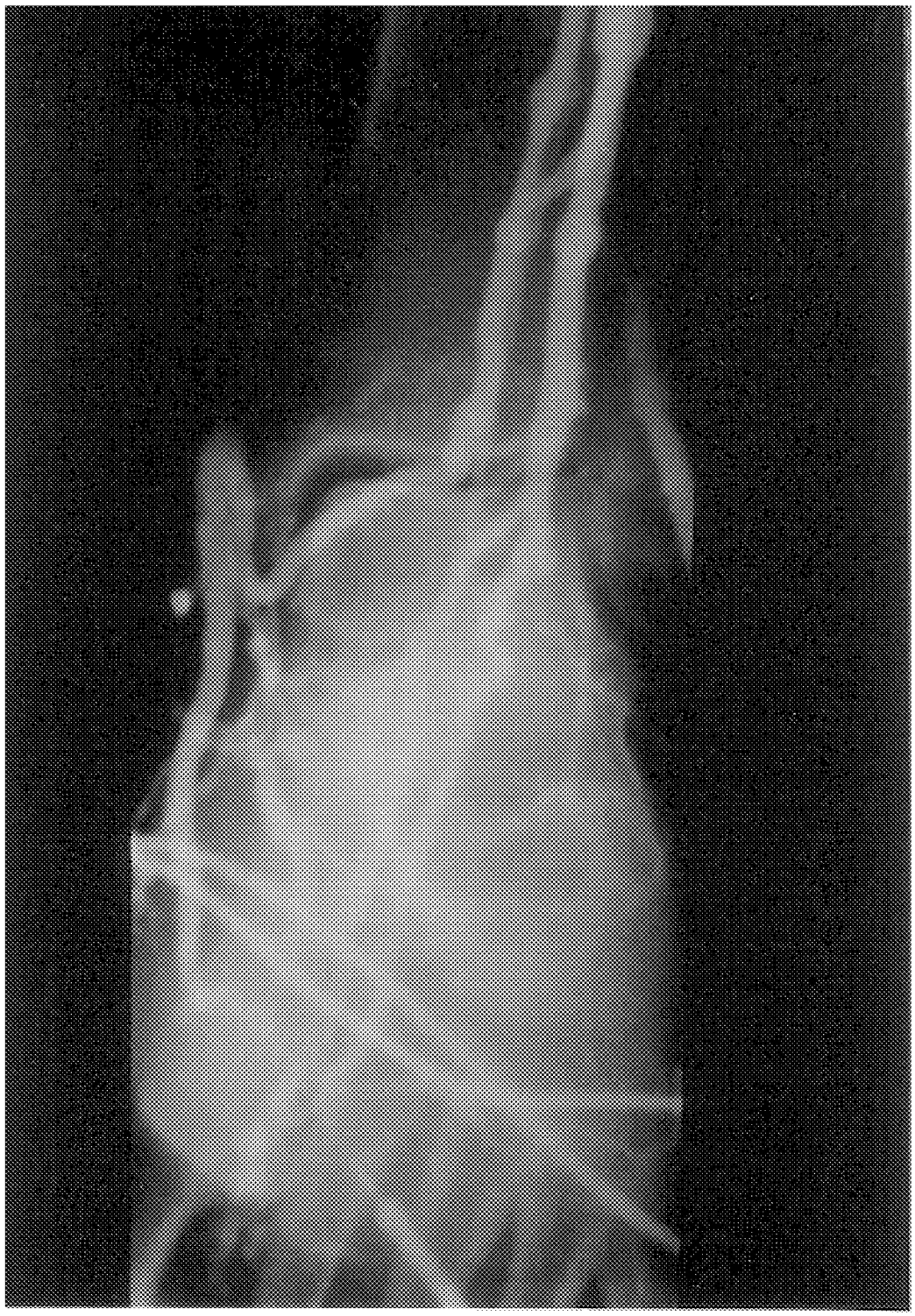
FIG. 3 is a photo of the foot.

Heparin is piggybacked into the urokinase line (FIG. 2). This delivers high heparin concentrations to the thrombus site along with urokinase. The purpose of this combination is to minimize thrombus propagation on the substrate of dissolving clot. Since thrombogenesis and thrombolysis represent opposing aspects of a very dynamic system, it is important to control clot formation during active lysis[28]. Since the venous occlusion is in the path of most resistance, systemic intravenous infusions of heparin deliver less effective concentrations of heparin to clotted veins. Other studies have reported that between 25% to 30% of patients presumed to be adequately covered with heparin or warfarin develop additional thrombus.[26] This may be due to stasis in the area of thrombosis where thrombogenic factors can override thrombus-inhibiting factors, again involving the concept of the path of least resistance. It is often difficult to achieve a therapeutic PTT in patients with large amounts of thrombus, but the PTT should be maintained between 40–90 seconds. It has been observed that as venous flow improves, the higher heparin dose required for systemic anticoagulation generally decreases. During follow-up venography, the heparin line should be switched to the systemic infusion site to maintain uninterrupted heparinization. Care must be taken to remember to return the heparin line to the UK line after the study to maintain optimal therapy. Heparin-induced sensitivity can result in thrombocytopenia. Although not common, it is observed for this potentially lethal phenomenon with serial platelet levels. A slight drop in platelets is seen frequently with urokinase therapy—probably a reflection of hydration. However, a precipitous drop or a delayed (5–6 days) and significant decrease should prompt appropriate evaluation and precautions.

EXAMPLE 6
Follow-up Studies

A follow-up venogram is obtained 12–24 hours after starting the infusion, and approximately once-a-day during the infusion. Because very few cases involve purely acute thrombus when treating extensive thrombosis, the flow-directed technique plus the catheter method generally require longer infusion times than a catheter-directed infusion in acute situations. Symptomatic improvement may occur within hours. However, lysis of subacute (5–14 days old) and chronic (>14 days) thrombus, which represents heterogeneous organized adherent clot, i.e., constantly providing a substrate for new thrombus, can require between 48–72 hours, and occasionally longer. Follow-up ascending venograms are performed via the stopcock without disturbing the pedal cannula. Problems, including phlebitis are rare. As the therapy progresses, occult bleeding can occur, especially in elderly patients. For this reason, follow-up checks are minimized to reduce transport-induced bruising and infusions are not prolonged if no progress occurs after 48–72 hours.

The point of termination is determined after consideration of clinical improvement (e.g., decreased limb pain and edema) and results of follow-up imaging studies. A perfect venogram, i.e., complete lysis, is not the goal in all cases given the high incidence of occult, chronic deep vein thrombosis in patients presenting with "acute" deep vein thrombosis. Rapid removal of the entire thrombus most frequently occurs with acute thrombus only. Although some authors consider less than total lysis a technical failure, sufficient outflow to prevent re-occlusion and restore outflow are the primary goals, particularly when treating subacute and chronic thrombosis. This can be achieved despite the presence of residual mural thrombus. In cases where extensive chronic clot does not lyse, stents are used in the iliofemoral area to augment lumen diameter and assure continued flow. Therefore, if venous flow is greatly improved, and clinical symptoms have decreased significantly, therapy is clinically adequate. Depending on the case, it is preferred to lyse thrombus associated with valves to prevent or mitigate damage caused by residual clot in these locations. No one knows if thrombus immediately damages valves, but the data suggest early lysis preserves valve integrity and prolonged thrombus presence correlates with damage to valves and valvular reflux.

There is probably a window of 1–5 days in which the thrombus is considered acute. There are varying degrees of thrombus organization and continued propagation. All these factors combine to affect valvular damage when the thrombus is not removed. Autolysis is not effective with extensive thrombus load and totally occlusive thrombus. Autolysis occurs most readily with sub-occlusive thrombus and single segment involvement. Urokinase can then be discontinued, maintaining heparin until conversion to oral anticoagulation is completed. It has been noted that in cases of subacute and chronic deep vein thrombosis, the most obvious improvement occurs between 24–72 hours after initiation of therapy. Often, the first follow-up study is disappointing in terms of venographic improvement, but as therapy is continued an inapparent threshold seems to be crossed, at which point both clinical and venographic improvement occur. Thrombolysis is a dynamic process and progress reflects removal of the "critical mass" of clot which has caused enough outflow obstruction to cause signs and/or symptoms of deep vein thrombosis. In older clots, a level of thrombus saturation with urokinase may take longer due to fibrous organization. However, fibrinogen will disrupt when exposed to urokinase, regardless of age. As the newer clot dissolves, a lumen enlarges and urokinase comes in contact with the older layers of thrombus. Thus, lysis, like thrombus formation, occurs in stages. Decrease in extremity pain generally is experienced sooner; i.e., within 8–24 hours, than a decrease in swelling. Although edema may begin to diminish, interstitial fluid can be slow to mobilize. As a result, significant decrease in limb circumference, particularly in the thigh, occurs over a period of days, not hours.

EXAMPLE 7
Safety

Prior to and throughout the procedure, thrombolytic therapy precautions are mandatory. These precautions include: no intramuscular injections; venipunctures for blood sampling are limited by placement of a dedicated heplock or use of the sheath port; the patient is placed on a pressure reduction surface or mattress; and a slide board and many hands should be used for patient transfer. Premedication with diphenhydramine or acetaminophen is not always necessary as the chills associated with high-dose pulse-spray arterial procedures are not observed with the prolonged venous infusions.

The management of thrombolytic therapy in patients with subacute and chronic thrombus requires more time and unerring diligence on the part of all staff. While different practitioners debate the value of fibrinogen levels, the lytic therapy was titrated to maintain a fibrinogen level >75% of baseline. It has been observed that the fibrinogen levels of most patients stabilize above this range when given a dose of 150,000 IU/hr, and need not be monitored as frequently once a stable level has been demonstrated. In the second case, fibrinogen levels decreased to an acceptable level at approximately 33% below baseline.

Baseline hemoglobin, platelet count, fibrinogen, prothrombin time (PT), and partial thromboplastin time (PTT) are obtained prior to lytic infusion and every 4–6 hours (every 6 or 8 hours for PT and PTT). In order to minimize decrease in hemoglobin secondary to phlebotomy, it is insisted that pediatric amounts be drawn and that any blood withdrawn to clear the line be reinfused. Fibrinogen levels may gradually decrease to 100–200 mg/dL in most patients. Urokinase infusion rates are adjusted downward if the fibrinogen drops to $\leq 25\%$ of baseline. Occasionally, the baseline fibrinogen will be lower than average, e.g., <200 mg/dL, but experience has shown that it rarely falls below 25% of baseline. It has been found that after an initial drop the fibrinogen level generally stabilizes if the urokinase infusion rate is $\leq 200,000$ IU/hr. For prolonged infusions, the interval of laboratory studies may be adjusted to every 6 hours. However, if the patient is elderly ($\geq 75$ years) or if there are relative risk factors, such as in a postoperative status of 2–3 weeks after hip repair or knee replacement, laboratory values should be checked every 4 hours and do regular limb measurements and site evaluations.

Following termination of the procedure, the patient must remain systemically heparinized until adequate, consistent PT/INR (international normalized ratio). An INR of 2–3 should be reached before heparin is discontinued and the patient is discharged. Warfarin anticoagulation is followed by the interventional radiologist or the referring physician and continued for 3–6 months. In patients with phlegmasia and extensive chronic deep vein thrombosis, long-term warfarin is recommended. It is recommended that the use of hip-high therapeutic support stockings (20–60 mm) in most patients, especially those with a history of previous deep vein thrombosis.

The following known complications should be avoided: (1) no intramuscular injections, as large hematomas can occur; (2) use of a slide board and many hands for transfers as trauma or bruising secondary to transfer from gurney to fluoro table can cause occult retroperitoneal hematomas, rectus sheath hematomas and large buttock hematomas; (3) lines and pumps should be labeled accurately to prevent errors; (4) all infusion concentrations and rates should be checked as pharmacies can make mistakes and rethrombosis or unwanted bleeding can occur if doses are not correct; all infusions should be kept on pumps not pressure bags and all lines must be kept patent as rethrombosis can occur if catheters are not continuously infused; and PTT should be rechecked if >200 as samples drawn from heparinized lines or veins in areas of poor flow give artificially high readings. The systemic heparin infusion should not be discontinued. Almost invariably, the PTT >200 is artifactual or represents a sample drawn too soon after a bolus injection or from an area with poor flow.

EXAMPLE 8

Case 1

Figure 4A:
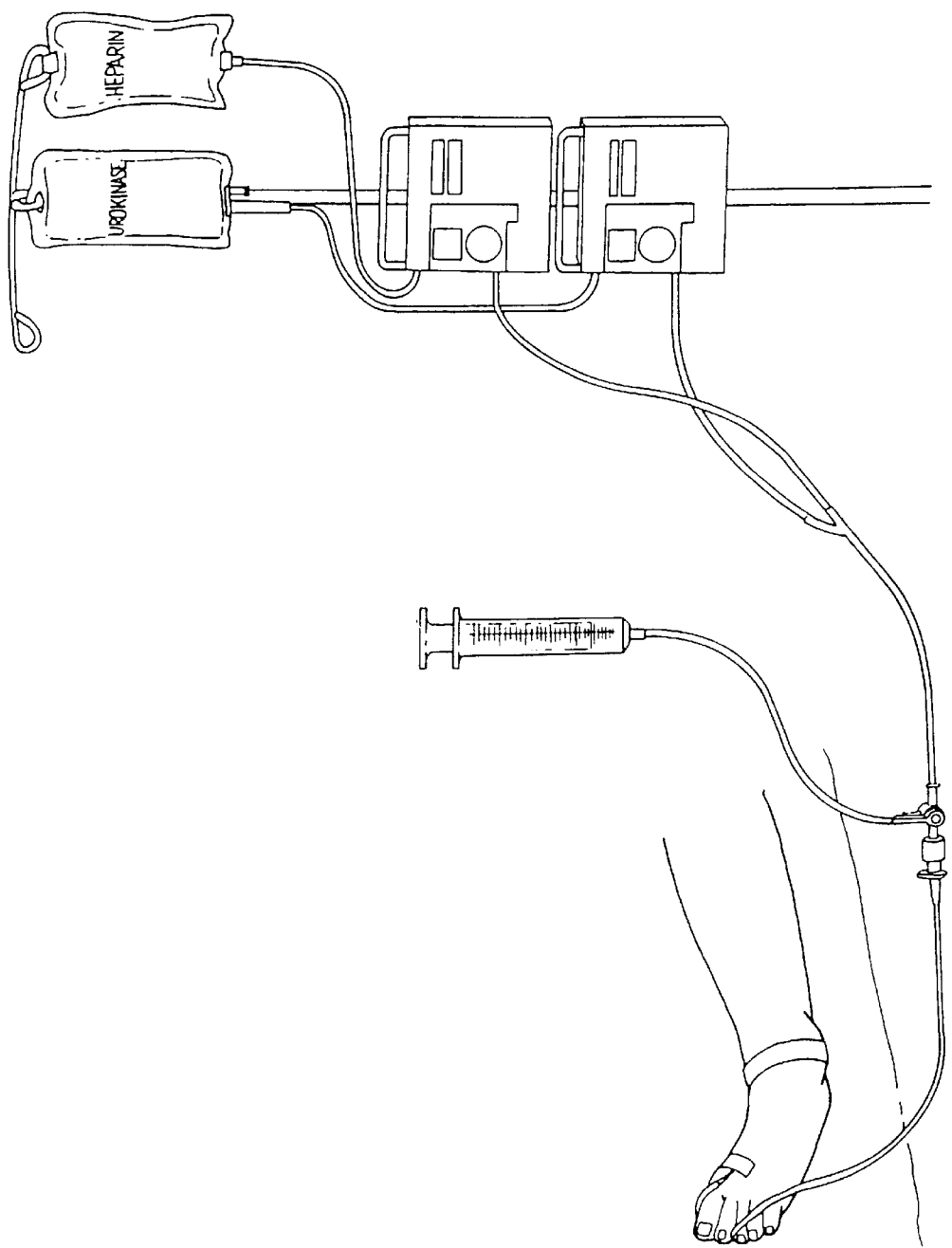
FIGS. 4A and 4B show the simultaneous urokinase and heparin flow-directed infusion.
Figure 4B:
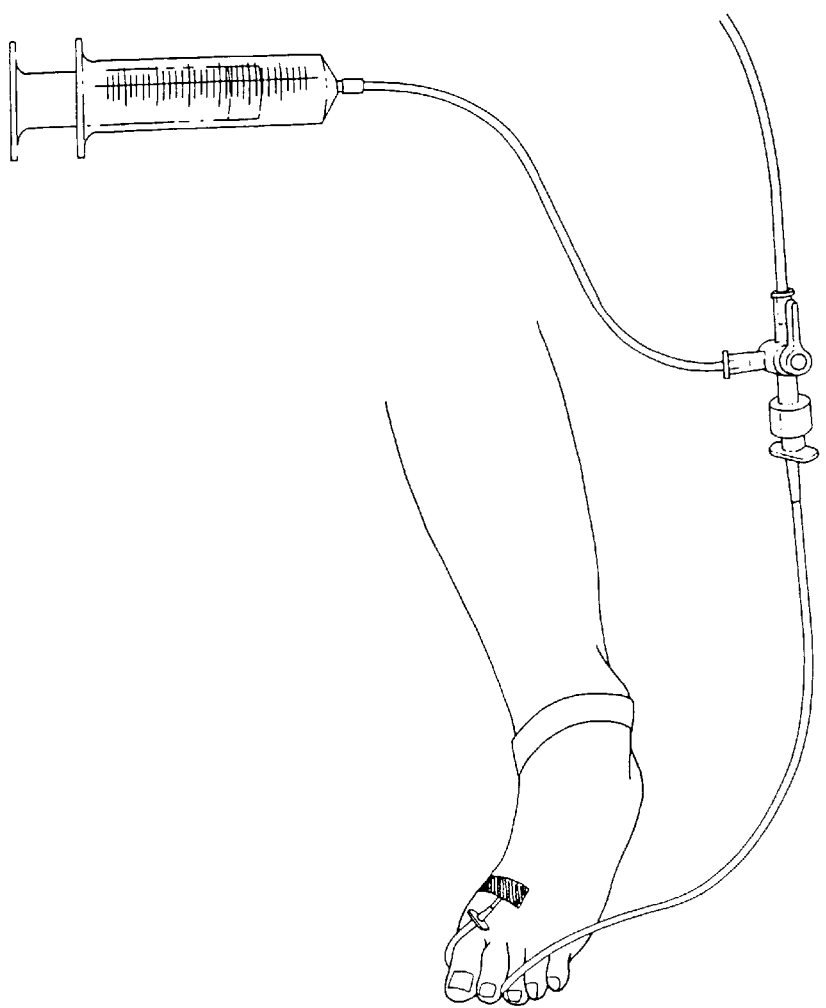

One week after falling and sustaining a soft tissue injury of the left knee, a 33-year-old woman presented an acutely swollen and tender left knee. A duplex ultrasound demonstrated thrombus in the left popliteal vein. Because of her youth and otherwise good health, she was referred to radiology for a diagnostic venogram and possible thrombolytic therapy. A baseline venogram (FIG. 4) showed a filling defect in the popliteal vein and poor filling of the posterior and anterior tibial system just below the knee.

Figure 5:
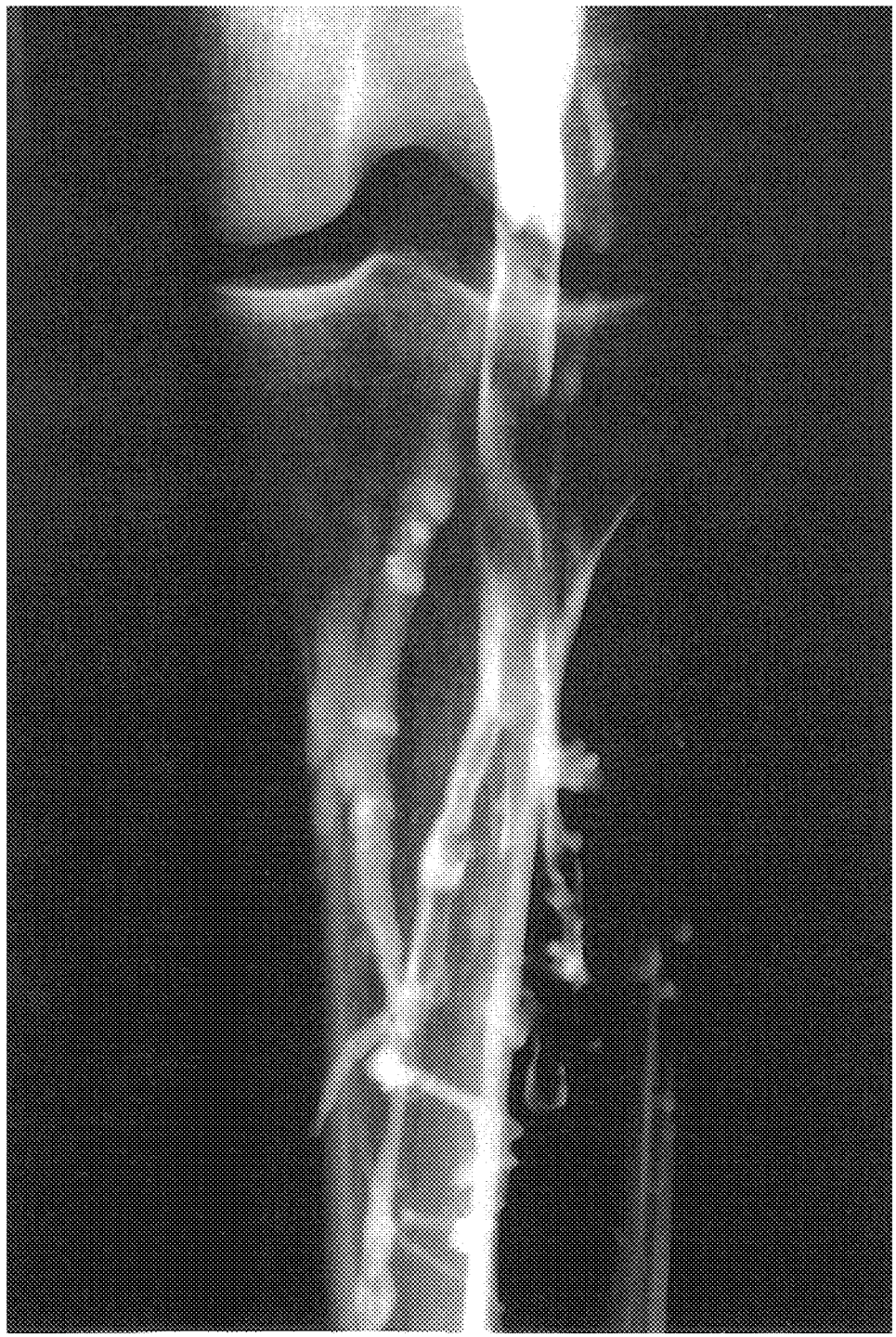
FIG. 5 shows a baseline venogram showing a patent saphenous; an acute thrombotic filling defect in the popliteal vein; and poor filling of the tibial peroneal veins.

Flow-directed pedal infusion of urokinase was conducted at 170,000 IU/hr for 18 hours. Systemic heparinization was combined with the urokinase infusion by using a three-way stopcock to deliver both heparin and the lytic agent to the deep venous system. A follow-up venogram was obtained the next day after a total urokinase dose of 3,060,000 IU. The filling defect in the popliteal vein was no longer present and there was improved visualization of the tibial systems (FIG. 5). Residual thrombus was noted in the anterior tibial vein near the venous confluence. During the period of urokinase infusion, the patient experienced no shortness of breath or other symptoms suggestive of pulmonary embolus. The significant improvement in venous outflow was accompanied by decreased calf tenderness and edema. The patient remained systemically heparinized until adequately anticoagulated on warfarin. Shortly after discharge on warfarin, the patient was ill with the flu, and after three days of nausea and vomiting, she developed a recurrent nonocclusive thrombus in the left popliteal vein. She was given a second short course of flow-directed urokinase to remove the thrombus, and was again discharged on warfarin. At 46 months follow-up, her left leg remained asymptomatic and ultrasound revealed normal venous outflow to the common femoral level with no evidence of residual filling defects. There was evidence of normal respiratory variation at all levels, normal proximal and distal augmentation, and no evidence of valvular incompetence.

This case emphasizes the need adequately to maintain anticoagulation in the post-thrombotic period. During this period the damaged endothelium that was responsible for the original thrombus remains thrombogenic for a variable length of time, making patients vulnerable for recurrent deep vein thrombosis if preventative techniques are not aggressive. During the patient's flu episode, her anticoagulation was no doubt compromised, thus allowing the same thrombotic forces that caused the original thrombus to generate a repeat thrombus.

The history of recent trauma in this case was not an absolute contraindication to lytic therapy. Careful observation of any potential bleeding site, in addition to frequent laboratory monitoring, would have identified any occult bleeding which could then be addressed by appropriate measures, including interval cessation of lytic therapy. In this instance, there was prompt resolution of the deep vein thrombosis with no evidence of further insult to the left knee. Moreover, follow-up ultrasound evaluation has continued to suggest maintenance of popliteal valve integrity. Limiting or preventing damage to the deep venous valves is a primary objective of thrombolytic therapy, along with restoring venous flow.

EXAMPLE 9

Case 2

Figure 6:
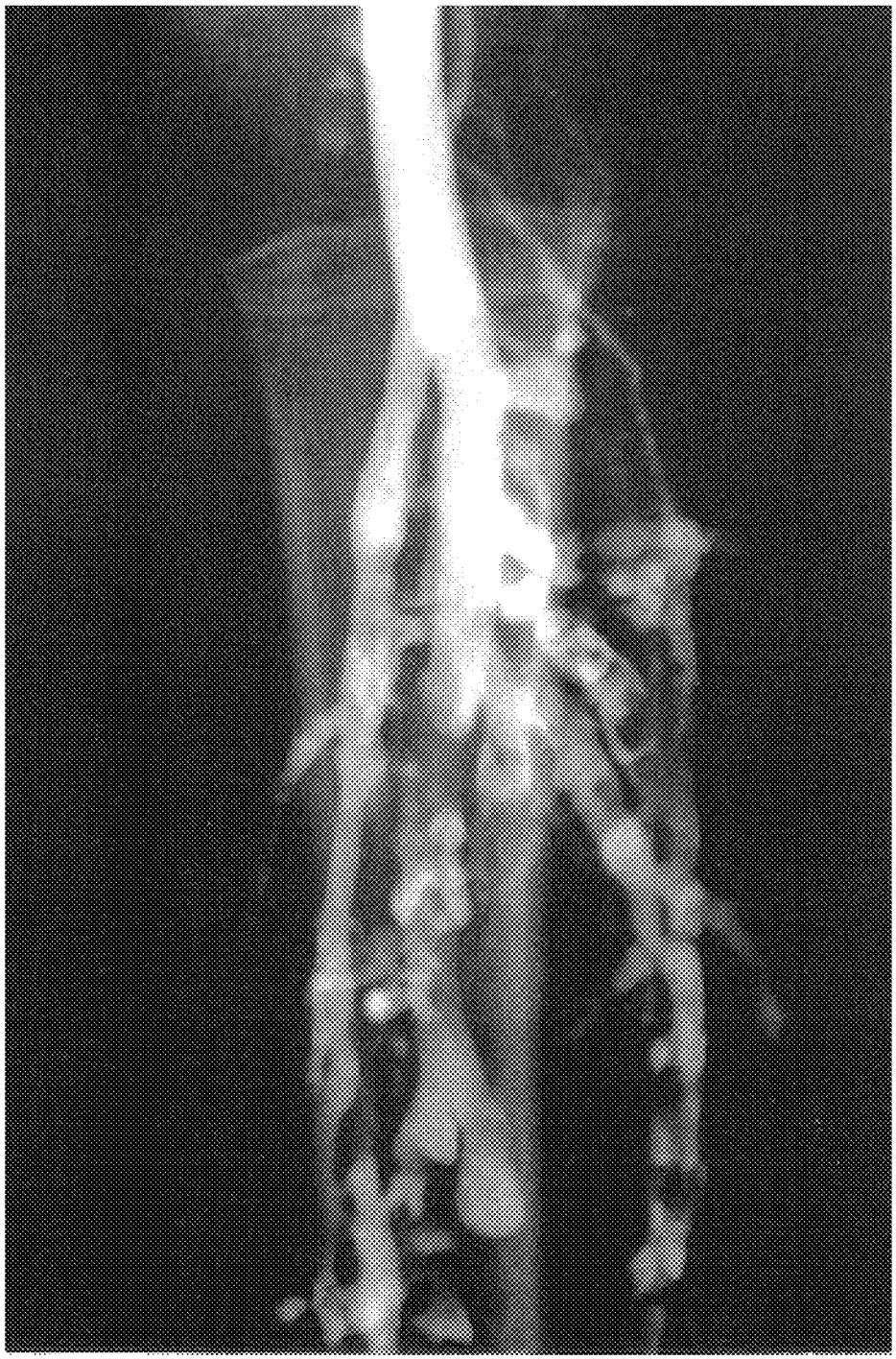
FIG. 6 shows a completion venogram showing resolution of the popliteal thrombus and re-established patency of the tibial veins with minimal residual thrombus in the anterior tibial.
Figure 8:
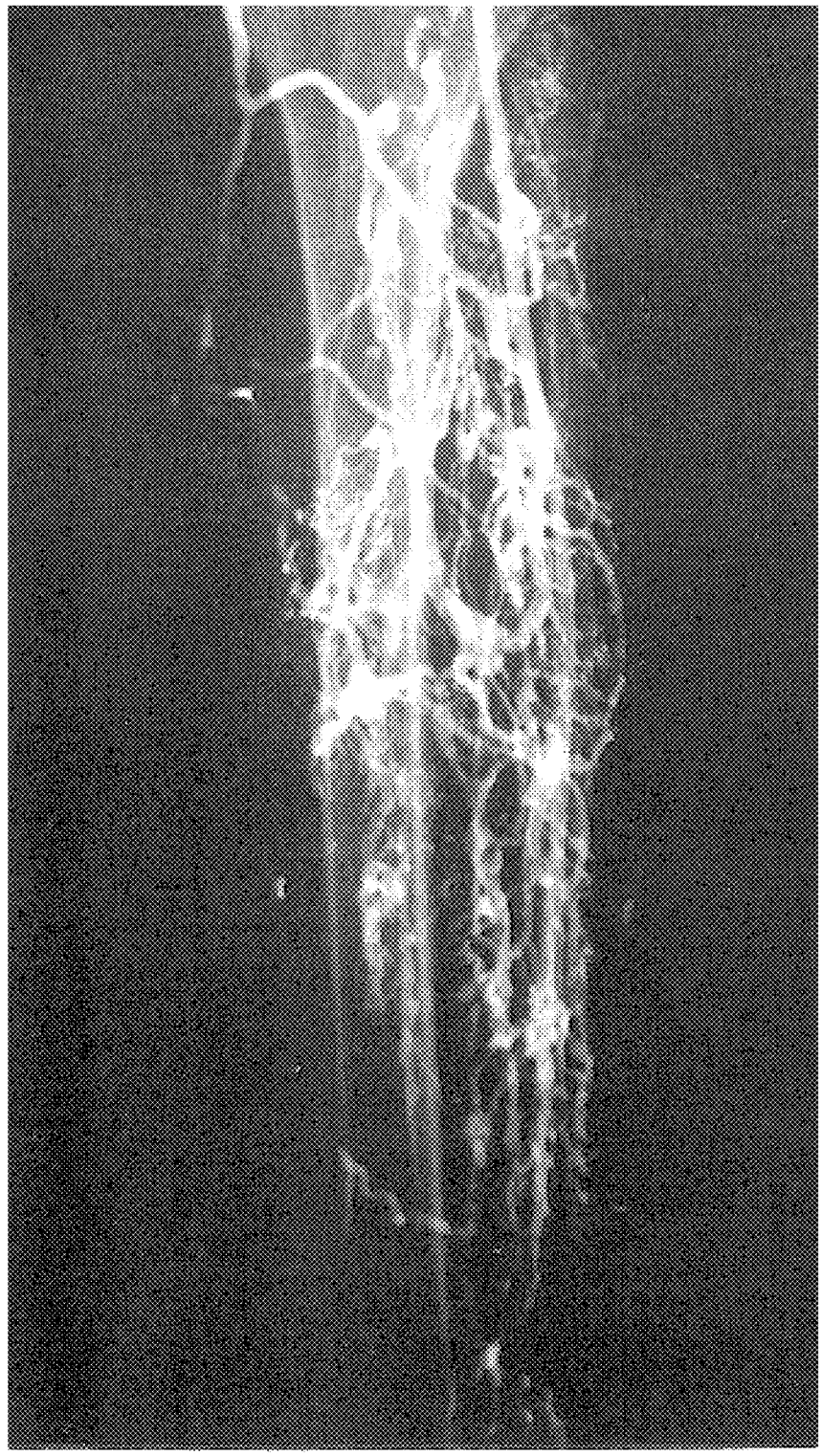
FIG. 8 demonstrates that following urokinase treatment, flow was re-established through the popliteal vein and a large number of deep infrapopliteal veins.

A 76-year-old woman fell and six weeks later was admitted for left-lower extremity deep vein thrombosis. She presented a history of progressive swelling and pain in the left leg which occurred over a period of weeks. The girth of the left calf measured 38 cm, compared to 31.5 cm on the right. A left lower extremity venogram demonstrated filling of the superficial venous vessels in the calf, with little evidence of a patent deep infrapoplitial system (FIG. 6). The popliteal vein was patent above the median accessory vein. The greater saphenous vein was visualized to the groin. Acute occlusive thrombus was suspected in the nonvisualized proximal superficial femoral vein as the confluence of the profunda femoris vein with the greater saphenous vein was widely patent with few collaterals (FIG. 8). The iliac system was patent. Despite evidence of occlusive thrombus in the thigh and calf, the main impedance to venous return appeared to be obstruction of the infrapopliteal deep system.

Figure 7:
FIG. 7 is a baseline venogram showing filling of superficial veins and very little contrast in the deep infrapopliteal system.
Figure 9:
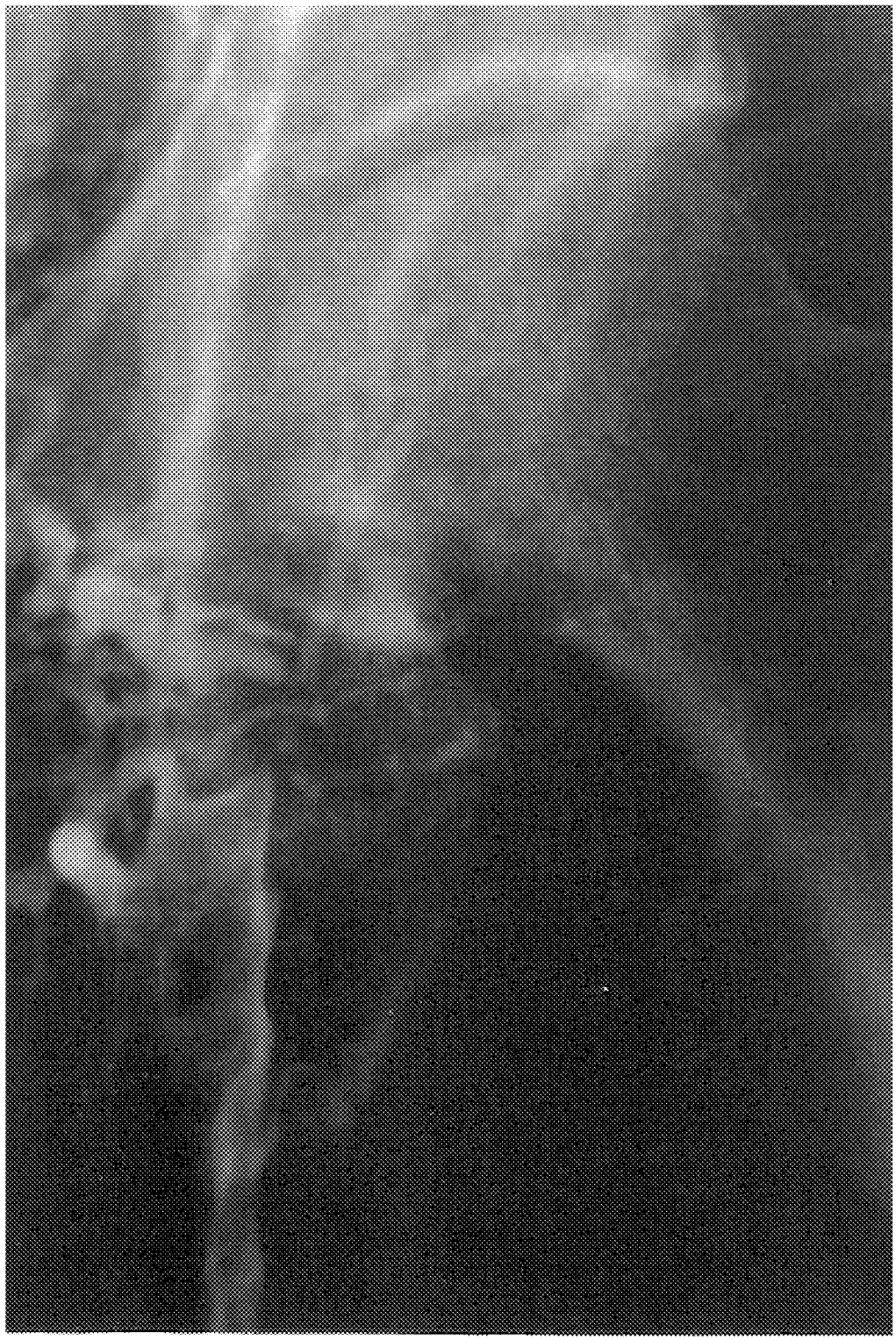
FIG. 9 shows acute occlusive thrombus in the nonvisualized proximal superficial femoral vein as the confluence of the profunda femoris vein with the greater saphenous vein.
Figure 10:
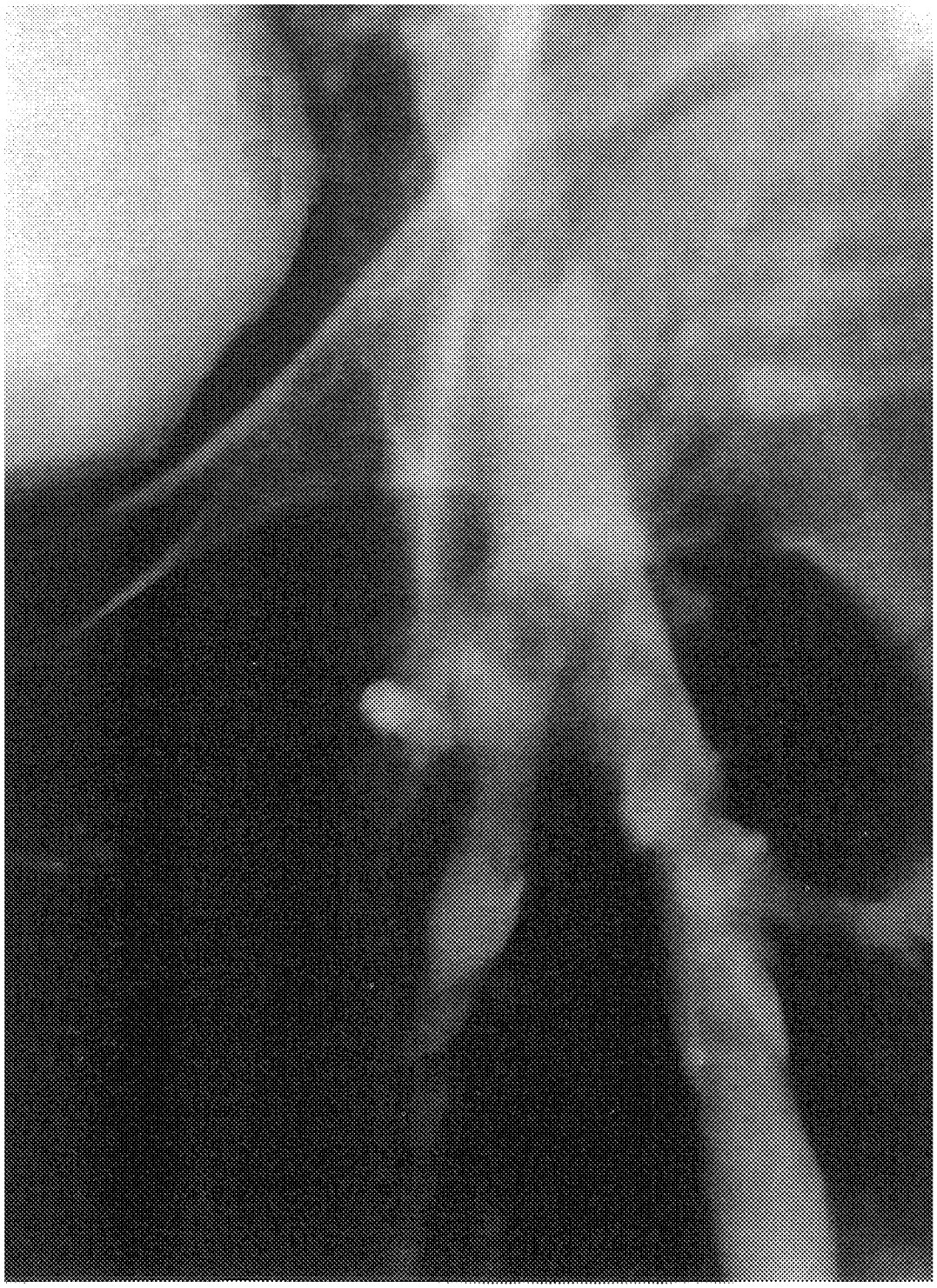
FIG. 10 shows the 24 hours post-treatment image of the superficial femoral vein with significantly increased despite residual thrombus.

Flow-directed pedal infusion of urokinase was initiated at 200,000 IU/hr. Systemic heparinization was administered through the urokinase line to inhibit propagation of thrombus during the lytic process. Fibrinogen levels fell from a baseline value of 330 mg/dL to a stable low of 120 mg/dL. The infusion was stopped twice for a short interval to allow the fibrinogen <120 mg/dL to rebound. No sign of bleeding was noted. A significant decrease in superficial vein thrombus was evident at 24 hours. Left calf circumference decreased from 38 cm to 34.5 cm in two days. Over the course of therapy, 11,200,000 IU urokinase over 64 hours, flow through the popliteal vein was gradually re-established and a large number of deep infrapopliteal veins became available for venous outflow (FIG. 7). The occluded femoral segments were also reopened completely (FIG. 9). No complications occurred. The patient was discharged after eight days of hospitalization, and continued warfarin anticoagulation for three months.

This patient has been closely followed for 6 years, and has had no left lower extremity pain or edema. This patient's long-term clinical status and absence of signs and symptoms of post-thrombotic syndrome are remarkable given the degree of chronic and acute deep vein thrombosis which was documented pretreatment. Re-established flow within the deep infrapopliteal system and the superficial femoral vein may have been partially accomplished by recanalization, without lytic therapy. However, many studies have shown that the degree of restored venous outflow, while unpredictable, is generally not sufficient to prevent intermittent edema and/or discomfort given the degree of obstruction and probable valvular damage which occurred in this patient. Her excellent long-term clinical outcome is in part a reflection of the degree to which her venous outflow more than usually seen with heparin therapy alone. Her immediate recovery allowed her to resume her normal activities and her capacity to lead a very active lifestyle remains a factor in her quality of life and overall clinical status.

EXAMPLE 10

Kit Instructions

A kit containing the elastic velcro tourniquets of the present invention is provided. The tourniquet is generally between, 14 inches and 22 inches in length. Each tourniquet comprises as many as 3 movable discs. The appropriate tourniquet length for the size of patient is chosen. An ankle and above-knee tourniquet can be used as indicated by the flow pattern.

The disc should be placed on the tourniquet on the back side of the velcro, approximately 4" from the end. A folded 4×4 gauze pad or the under-the-disc pad/cap is used and the disc is placed over the saphenous vein, just above the medial malleolus. The tourniquet is wrapped around the ankle so the disc pressure compresses the saphenous flow enough to redirect flow into the deep venous system. Flow should be confirmed fluoroscopically. The skin is marked clearly to place the tourniquet and the disc position properly to assure accurate replacement every hour. The tightness of the tourniquet always should be checked to ensure that the dorsalis pedis pulse does not change. The patient should not feel any tingling or numbness. When confirming the flow pattern fluoroscopically, one should check for extravasation at the IV site. The tourniquet should be released for 10–15 minutes every hour during UK infusion.

The advantages of the flow-directed method via pedal access are: (1) the concentration of lytic agent at the site of the deep vein thrombosis is higher than that achievable with a systemic infusion; (2) the systemic concentration of lytic agent reaching remote sites is lower and this results in fewer systemic lytic effects that result in bleeding; (3) with the provision of advantages 1 and 2, the longer infusion times necessary to address the thrombotic burden in the deep veins of the legs are facilitated; and (4) effective lytic therapy can be achieved without a catheter in selected cases.

Flow-directed thrombolytic therapy is possible because of the multitude of venous channels that maintain imperceptible flow, thus delivering urokinase to veins occluded with thrombus. Also, since venous thrombus organizes more slowly than arterial thrombus, a new or less organized clot is often present in the midst of chronic venous occlusions. Removal of the new clot load increases venous outflow and permits exposure of the thrombolytic agent to an underlying thrombus that is older, but still contains a fibrin substrate that is susceptible to lytic therapy. This pattern of anatomy and pathology is reflected in the clinical progress seen in patients with subacute and chronic thrombus where significant lysis does not occur until 24–48 hours after initiation of therapy. In contrast, acute venous thrombosis can resolve within a few hours. Acute thrombus is generally defined as <3–5 days, subacute 5–14 days, and chronic >14 days. However, duration of symptoms and signs of deep vein thrombosis do not always correlate directly to age of the thrombus. In most cases, there is a heterogeneous clot that varies in degree of organization. This was probably the case with the second patient (Example 9). Given her history, the most likely diagnosis was subacute or chronic deep vein thrombosis with acute exacerbation. The vague and intermittent discomfort with progressive edema, which became significantly worse in a short period of time, was consistent with the continued propagation of thrombus despite development of collateral flow. Thrombosis and intrinsic thrombolysis are part of a very dynamic process which changes constantly the configuration and composition of a venous thrombosis. Patients often have temporary collateral compensation and thereby remain relatively asymptomatic until a critical mass of thrombus obstructs enough outflow to cause symptoms. Because prior experience with systemic thrombolytic infusions has produced poor results in patients with delayed diagnosis, it is generally believed that lytic therapy is not effective in thrombi older than 7 days.[28] Of course, with systemic infusions from an upper extremity venous infusion site, the thrombolytic agent is not delivered to the obstructive thrombus efficiently enough to produce satisfactory lysis. Flow-directed or catheter-directed techniques allow urokinase to reach thrombus in sufficient concentration to dissolve clot and increase outflow. Although catheter delivery may accelerate lysis of superficial femoral vein clot, when multiple infrainguinal and infrapopliteal segments are involved, catheter-directed therapy alone may not be sufficient. If the outflow channels are opened but the inflow remains compromised by clot, there may be inadequate flow to maintain patency or relieve symptoms. Furthermore, removal of clot from popliteal and infrapopliteal sites may be the key to preservation of reflux and, later, edema and pain.

Urokinase infusion via a pedal infusion site can be directed by the purposeful use of tourniquets to maximize delivery to the occlusive thrombus, opening occluded deep veins in which flow may not be documented by venography or ultrasound. The utilization of the flow-directed method can make thrombolytic treatment of the acute thrombus a more readily available and safe option to patients in areas where a physician experienced in catheter placement is not available.

Adherence to safety precautions and principles of flow dynamics can produce excellent cost-effective outcome. Minimizing damage to valves is an objective of therapy in acute deep vein thrombosis, but preserving valves is clearly not the goal in chronic cases. Nevertheless, in both situations, removal of obstructive thrombus optimizes venous outflow and significantly contributes to clinical improvement. Keeping thrombus form re-forming is as important as its initial removal.

The following references were cited herein:
1. Sharma, GVRK et al., Thrombolytic therapy in deep vein thrombosis., In: *Thrombosis and Urokinase*, Paoletti R, Serry S, eds. Academic Press; 181–189, 1977.
2. Graor, R A et al., *Ann Vasc Surg;* 1:524–528, 1987.
3. Robertson, B R et al., *Acta Chir Scand;* 134:203–208, 1968.
4. Elliot M S et al., *Br J Surg;* 66:838–843, 1979.
5. Arnesen H et al., *Acta Med Scand;* 211:65–68, 1982.
6. Marder V J, *Ann Intern Med;* 93:136–137, 1980.
7. Killewich L A et al., *J Vasc Surg;* 9:89–97, 1989.
8. Meissner M H et al., *J Vasc Surg;* 18:596–608, 1993.
9. Katzen B T et al., *J Vasc Surg;* 1:718–22, 1984.
10. McNamara T O et al., *AJR;* 144:769–775, 1985.
11. van Breda A et al., *Radiology;* 165:109–111, 1987.
12. LeBlang S D et al., *JVIR;* 3:474–483, 1992.
13. Becker G J et al., *Radiology;* 149:419–423, 1983.
14. Fankuchen E I et al., *Cardiovasc Intervent Radiol;* 7:90–93, 1984.
15. Druy E M et al., *J Vasc Surg;* 2:821–827, 1985.
16. Harke H et al., *Intensive Care Med;* 13:39–45, 1987.
17. Machleder H I, *Semin Vasc Surg;* 3:1–8, 1990.

18. Iaccarino V, Local venous thrombolysis., In: *Interventional Radiology,* Dondelinger R F, Rossi P, Kurdziel, Wallace F, eds. 1990, Thieme Medical Publishers, Inc., New York; 653–657.

19. Okrent D et al, *JVIR;* 2:195–197, 1991.

20. Molina J E et al., *Vascular Surgery,* Oct. 630–637, 1992.

21. Robinson D L et al., *AJR;* 160:1288–1290, 1993.

22. Semba C P et al., *Radiology;* 191:487–494, 1994.

23. Comerota A J et al., *J Vasc Surg;* 20:244–254, 1994.

24. Martin M et al., *Angiology, Feb.,* 143–148, 1994.

25. Marder V J et al., *J Lab Clin Med;* 5:1018–29, 1977.

26. Krupski W C et al., *J Vasc Surg;* 12:467–75, 1990.

27. O'Reilly R A, Anticoagulant, Antithrombotic, and Thrombolytic Drugs. In: *The Pharmacological Basis of Therapeutics.,* Gilman et al., eds., 7th ed., New York: Macmillan; 1985: chap 58.

28. Sherry S et al., *Ann Intern Med;* 93:141–144, 1980.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples, along with the methods, procedures, treatments, molecules, and specific compounds described herein, are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for treating deep vein thrombosis, comprising the steps of:

placing an intravenous needle in a vein in an area to be treated;

determining a pattern of venous blood flow in said area to be treated;

securing a tourniquet around said area to be treated, said tourniquet comprising: a band, said band having a width and a length, and a first end and a second end, wherein said first end and said second end have means for adjustably connecting to one another, wherein said band is flexible along the length of said band, and wherein said band is adapted to encircle an appendage; and a disc, wherein said disc is comprised of a substantially hard, non-compressible material, wherein said disc comprises a surface for contacting the appendage, an entirety of said disc being cylindrically shaped and said disc is adjustably connected to said band, wherein said band is adapted to be secured around the appendage such that the disc applies sufficient area pressure to restrict and redirect sub-surface venous blood flow and an intravenously-administered thrombolytic agent, thereby promoting thrombolysis, thereby alleviating deep vein thrombosis in the appendage; wherein said disc of said tourniquet is positioned over said vein so as to apply pressure to said vein;

checking re-direction of blood flow through said area to be treated;

infusing said vein through said needle;

releasing said tourniquet after an appropriate period of time; and re-securing said tourniquet after an appropriate period of time.

2. The method of claim 1, wherein said determining step is performed via fluoroscopy.

3. The method of claim 1, further comprising the step of marking said area to be treated after said securing step and said checking step.

4. The method of claim 1, wherein said releasing step is performed 30–60 minutes after said securing step.

5. The method of claim 4, wherein said releasing step is performed 50 minutes after said securing step.

6. The method of claim 1, wherein said re-securing step is performed after 5–30 minutes after said releasing step.

7. The method of claim 1, wherein said infusing of said vein is with urokinase.

\* \* \* \* \*